(12) United States Patent
Hacker et al.

(10) Patent No.: US 8,663,157 B2
(45) Date of Patent: Mar. 4, 2014

(54) FLUID MANAGEMENT SYSTEM

(75) Inventors: Randall Hacker, Naples, FL (US);
Ronald Seese, Naples, FL (US);
Terrance J. Mclaughlin, Naples, FL (US); Adam Mankowski, San Antonio, TX (US); Edwin W. Floyd, Bonita Springs, FL (US); James A. Tebo, Naples, FL (US); Milton D. Frank, Bergenfield, NJ (US); Sheshin Yamin, Warren, NJ (US)

(73) Assignee: Arthrex, Inc., Naples, FL (US)

( * ) Notice: Subject to any disclaimer, the term of this patent is extended or adjusted under 35 U.S.C. 154(b) by 7 days.

(21) Appl. No.: 13/527,278

(22) Filed: Jun. 19, 2012

(65) Prior Publication Data

US 2012/0310161 A1    Dec. 6, 2012

Related U.S. Application Data

(62) Division of application No. 12/562,881, filed on Sep. 18, 2009, now Pat. No. 8,206,342.

(60) Provisional application No. 61/136,628, filed on Sep. 19, 2008.

(51) Int. Cl.
*A61M 31/00* (2006.01)

(52) U.S. Cl.
USPC ........................................................ 604/67

(58) Field of Classification Search
USPC ........ 604/29, 30, 31, 34, 35, 65, 67, 118, 151
See application file for complete search history.

(56) References Cited

U.S. PATENT DOCUMENTS

| | | | |
|---|---|---|---|
| 4,902,277 A | | 2/1990 | Mathies et al. |
| 4,976,590 A | * | 12/1990 | Baldwin .......................... 417/53 |
| 5,000,733 A | | 3/1991 | Mathies et al. |
| 5,131,823 A | | 7/1992 | Guignard |
| 5,167,659 A | | 12/1992 | Ohtomo et al. |
| 5,319,979 A | * | 6/1994 | Abrahamson ................... 73/745 |
| 5,520,638 A | | 5/1996 | O'Quinn et al. |
| 5,649,808 A | * | 7/1997 | Gruszecki et al. .............. 417/63 |
| 5,964,746 A | | 10/1999 | McCary |
| 5,991,142 A | | 11/1999 | Appelbaum et al. |
| 8,206,342 B2 | * | 6/2012 | Hacker et al. ................... 604/67 |
| 2007/0078370 A1 | | 4/2007 | Shener et al. |
| 2008/0154095 A1 | | 6/2008 | Stubkjaer et al. |

FOREIGN PATENT DOCUMENTS

| | | |
|---|---|---|
| EP | 2165720 A1 | 3/2010 |
| JP | 11193785 A * | 7/1999 ................ F04C 5/00 |

OTHER PUBLICATIONS

"Stepper Motor," Wikipedia Foundation, Inc. http://en.wikipedia.org/wiki/Stepper_motor, Dec. 12. 2013.
"IEC Connector." Wikipedia Foundation, Inc., http://en.wikipedia.org/wiki/IEC_connector, Dec. 12, 2013.

\* cited by examiner

*Primary Examiner* — Aarti B Berdichevsky
(74) *Attorney, Agent, or Firm* — Dickstein Shapiro LLP

(57) ABSTRACT

A fluid management system with a detection circuit for detecting whether an attached surgical device is operational. The fluid management system changes at least one operation mode when the surgical device is detected as being operational. The fluid management system may include inflow, outflow, or inflow/outflow capabilities, and monitors at least one signal characteristic of an AC power signal provided to the surgical device.

6 Claims, 12 Drawing Sheets

FLUID MANAGEMENT SYSTEM

This is a divisional of application Ser. No. 12/562,881, filed Sep. 18, 2009, now U.S. Pat. No. 8,206,342, which claims the benefit of U.S. Provisional Application No. 61/136,628, filed Sep. 19, 2008, the entirety of which is hereby incorporated by reference.

BACKGROUND

1. Field of the Invention

The present invention relates to a system for managing fluid inflow and/or outflow to an operative site (e.g., a knee joint), while also detecting whether a surgical device (such as a shaver) connected to the system is in an operational state.

2. Description of the Related Art

During arthroscopic surgery, it is necessary to have a clear field of vision, which requires reduction of blood flow into the operative site, quick removal of debris, and distension of joint spaces sufficient to maneuver surgical instruments. Fluids introduced under pressure into the operative site achieve these objectives. One such prior art fluid management system is the arthroscopy infusion pump described in U.S. Pat. No. 5,520,638, assigned to Arthrex, Inc., the disclosure of which is incorporated by reference in its entirety.

Prior art fluid management systems typically utilize one tube to deliver fluid under pressure to the operative site, a second tube to remove the fluid from the operative site while the surgical device is not being operated, and a third tube to remove the fluid from the operative site while the surgical device is being operated. That is, the fluid enters the operative site through the first tube and exits the operative site through one of the second or third tubes. Both the second and third tubes are simultaneously connected to the operative site. When the surgical device is not being operated (e.g., when a shaver trigger on a shaver is not depressed), the fluid exits the operative site through the second tube, referred to as a "cannula tube." When the surgical device is being operated (e.g., when the shaver trigger is depressed), then the fluid exits the operative site through the third tube, referred to as a "device tube" (or, when the surgical device is a shaver, a "shaver tube").

In some conventional fluid management systems that are configured for use with a particular surgical device, switching of the outflow path is designed to occur automatically with operation of the surgical device. When a particular surgical device is designed for use with a particular fluid management system, the controls of the two may simply be integrated to provide this feature. Surgical devices from many different manufacturers and with many different part numbers, however, may be used in conjunction with such fluid management systems. In fact, it is common for a surgeon to have a preferred surgical device—such as a preferred shaver console and/or hand piece—that may or may not be the same manufacturer as that of the fluid management system. It is also common for a surgical device from one manufacturer to be used with a fluid management system from another manufacturer. In such situations, compatibility problems can arise. For example, the fluid management system of one manufacturer is not able to detect when an attached surgical device from another manufacturer is being operated. Thus, the fluid management system may not be capable of automatically switching between the cannula tube and the device tube for outflow from the operative site, without the use of a customized detection device.

For example, one such prior art fluid management system that includes a detection device is the FMS Duo manufactured by DePuy Mitek, and as described in U.S. Pat. Nos. 4,902,277, 5,000,733 and 5,131,823, the contents of which are incorporated herein by reference. The FMS Duo utilizes a shaver detection device that is specific to each shaver hand piece cord. The shaver detection device has a male/female connector that must be custom made for each shaver hand piece model on the market. Thus, when a new shaver hand piece is developed by a given manufacturer, a new shaver detection device must also be developed by DePuy Mitek in order to properly operate the fluid management system for its intended purpose.

Accordingly, there exists a need in the art for an improved fluid management system which does not require a separate custom-made detection device for each surgical device on the market.

Also in conventional fluid management systems, switching between the operational and non-operational outflow fluid pathways (i.e., the cannula and device tubes) is physically accomplished by a pinch mechanism, commonly including a rotating wheel located between the two tubes. The wheel is configured to switch between restricting—or "pinching off"—one of the two tubes, while allowing fluid to travel through the other. This configuration results in a complicated procedure for connecting the tubes to the fluid management system. For example, conventional pumps require that the user install one outflow tube first, press a pinch button to move the pinch mechanism, and then load the second outflow tube.

Accordingly, there exists a need in the art for an improved fluid management system and method for easing installation and replacement of outflow tubes.

The pressure at which fluids are introduced at an operative site is preferably stable over a period of time, and capable of being specified depending upon the use. Prior art systems include pressure sensors to detect an inflow pressure at the operative site, but this requires additional intrusive components at the operative site. The pressure can instead be estimated based upon the pressure at the output of an inflow pathway of an inflow/outflow pump. However, these inflow pressure estimates can be inaccurate, especially when a surgical device is operational at the operative site.

Accordingly, there exists a need in the art for improved devices and methods for compensating for variations in pressure levels at the operative site.

SUMMARY OF THE INVENTION

The present invention fulfills the needs noted above by providing a fluid management system with a detection circuit that monitors signal characteristics of an AC power signal provided to an attached surgical device to detect when the surgical device is being operated (i.e., when the device is operational). In one embodiment, the surgical device is a shaver, and the fluid management system is an inflow/outflow pump. When the fluid management system detects that the surgical device is being operated, it can automatically adjust operation modes accordingly. For example, when the detection device described herein detects that the device is operational, the fluid management system can switch the outflow path to an operational outflow path, and also increase the fluid flow rate and/or pressure to help eject debris that may be generated during use of the surgical device. When the fluid management system detects that the surgical device is no longer being operated, the fluid management system again adjust operation modes—i.e., switches the outflow back to the non-operational outflow path and the flow rate and/or pressure back to the non-operational rate.

The detection circuit is coupled between the power cord of the surgical device and an interface for an AC power cord on the fluid management system. The detection circuit detects a change between a non-operational level of one or more signal characteristics (i.e., when the surgical device is not being operated) and operational level of the signal characteristics (i.e., when the surgical device is being operated). The fluid management system can utilize a standard IEC 320 connector that connects to the power receptacle or power cord of many conventional surgical devices, such as the console of most shaver devices; thus there is no need for a customized detection device for every brand or variation of surgical device on the market. The fluid management system may also be programmed to detect the manufacturer and part number attached thereto based upon the current load measured during the operational state.

A rotating motor can be used to operate a wheel configured to switch the outflow fluid path between the non-operational path (i.e., a cannula tube) to the operational path (i.e., a device tube). The rotating motor may be, for example, a stepper motor, providing precise rotation. The rotating motor can be configured to rotate to the center of its axis during loading and unloading of the outflow tubes, rather than being aligned to pinch off one of the outflow tubes. This design improves loading of the tubes, and allows for use of a detachable cassette holding the tubes.

The fluid management system can also be configured to estimate the fluid pressure at the operative site, and may utilize a pressure algorithm to estimate the pressure based upon the operational flow rate. The pressure algorithm may estimate the pressure without the need for taking an actual pressure measurement at the operative site. This eliminates the need for an additional incision for a pressure monitor as required by prior art fluid management systems, while also compensating for varying conditions at the operative site. The pressure algorithm can be adjusted according to the operational state as well as the inflow and/or outflow rate of the fluid management system.

DETAILED DESCRIPTION OF PREFERRED EMBODIMENTS

Figure 1:
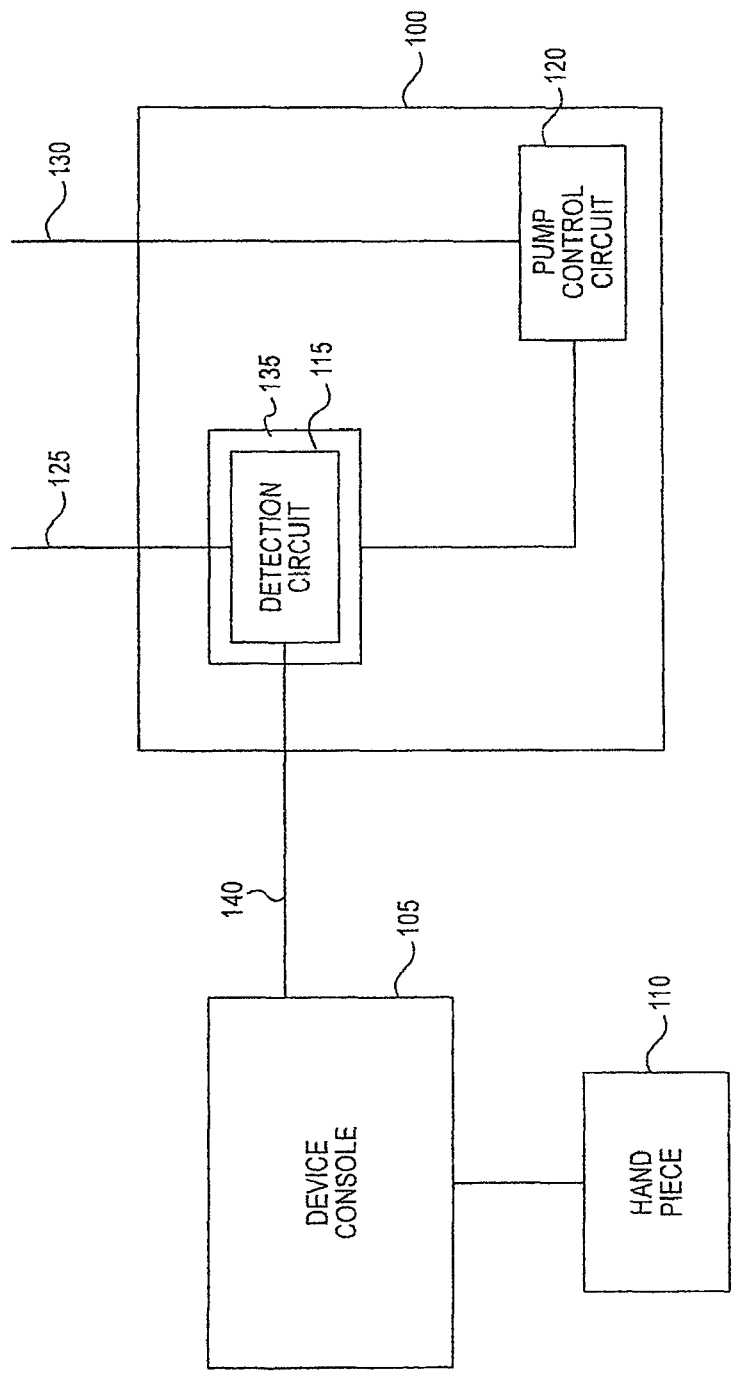
FIG. 1 illustrates a block diagram of a fluid management system and connected surgical device, in accordance with an exemplary embodiment of the invention.

The present invention is directed to a fluid management system with a detection circuit and methods for controlling the same. Referring now to the drawings, where like elements are designated by like reference numerals, FIGS. 1-11 illustrate the apparatus and methods of the present invention.

Referring to FIG. 1, a fluid management system 100 is illustrated, in accordance with an exemplary embodiment of the invention. In one preferred embodiment, fluid management system 100 is operationally similar to the Continuous Wave III Arthroscopy Pump (Part No. AR-6475), as manufactured by Arthrex, Inc., and also similar to the arthroscopy infusion pump described in U.S. Pat. No. 5,520,638. However, fluid management system 100 includes additional features, some of which are described further below, that are not found in the prior art.

Fluid management system 100 provides fluids under pressure to an operative site, and/or removes fluids and other materials from the operative site, such as via an inflow pump for providing fluid under pressure to an operative site, an outflow pump for removing fluid from the operative site, or an inflow/outflow pump. Fluid management system 100 may provide both inflow and outflow fluid management simultaneously, but need not include both functions.

If configured to provide outflow operations, fluid management system 100 includes at least an operational path (i.e., the device tube) and a non-operational path (i.e., the cannula tube). If configured to provide inflow operations, fluid management system 100 includes an inflow pathway to provide fluid at a relatively stable flow rate. Suction at the outflow pathway and pressure at the inflow pathway can be provided and controlled by, for example, variable-speed peristaltic motors, as are known in the art. The inflow and/or outflow pump components of fluid management system 100 receive power via power cord 130.

Fluid management system 100 is coupled to a surgical device. The surgical device may include a hand piece 110 coupled to a device console 105; for example, a shaver hand piece and shaver console, respectively, as is known in the art. It should also be understood that a surgical device for use with embodiments of the fluid management system described herein need not include a console and hand piece, but may be any surgical device known in the art that has controllable operation and is desirable for use with a fluid management system.

The console 105 of the surgical device is coupled to the fluid management system by power cord 140, which acts as a conduit for an AC signal to the surgical device. Power cord 140 may be any known power cord for surgical devices, and may be a standard power cord such as an IEC 320 power cord, as is known in the art. When the surgical device is not being operated (e.g., when a trigger on hand piece 110 is not depressed), an AC signal having first signal characteristics (i.e., a steady state signal) is supplied to console 105 via power cord 140. However, when the surgical device is being operated (e.g., when the trigger is depressed), then an AC signal having different signal characteristics (i.e., typically including signal characteristic with increased levels than the steady state levels) is supplied to console 105 via power cord 140.

Fluid management system 100 conducts operations—such as inflow, outflow, and/or pressure estimation—according to operation modes such as, but not limited to, inflow pressure, inflow flow rate, outflow flow rate, outflow fluid path, and pressure algorithm. One or more of the operational modes are desirably adjusted when an attached surgical device is in an operational state versus a non-operational state.

Fluid management system 100 also includes a detection circuit 115. Detection circuit 115 is isolated (indicated by element 135), and preferably galvanically isolated, from other circuitry within fluid management system 100 so as to not compromise the electric measurements being taken. Detection circuit 115 can be located integral to the same structure as the inflow/outflow pump components of fluid management system 100, or may be located external to this structure, for example on an external board. Power can be provided to detection circuit 115 by a separate power cord 125, or from the inflow/outflow pump via an internal connection or a second power cord.

Detection circuit 115 detects changes in the operational status of the attached surgical device by detecting changes in the power provided to the surgical device via cord 140. Detection circuit 115 monitors levels of one or more signal characteristics of the AC signal provided to power cord 140, including, but not limited to, current, voltage, noise level, and/or power. Because detection circuit 115 is provided as part of fluid management system 100 rather than in power cord 140, detection circuit 115 does not rely on the power cord of the surgical device, and can detect changes in operational status of various connected surgical devices by different manufacturers.

Fluid management system 100 can automatically change or adjust various operation modes according to the detection. For example, when detection circuit 115 detects that the surgical device is not being operated, it can provide a signal to pump control circuit 120 to control the outflow so that the fluid exits the operative site from the non-operational path (i.e., the cannula tubing) and also controls the inflow and outflow rates to be non-operational flow rates. When detection circuit 115 detects that the surgical device is being operated, it can provide a signal to pump control circuit 120 to control the outflow so that the fluid exits the operative site from the operational path (i.e., the shaver tubing) and also increases the inflow and outflow rates to be pre-set operational flow rates. Other operation modes, including inflow pressure and a pressure algorithm used to estimate pressure at the operative site, can also be adjusted or changed accordingly.

Figure 2A:
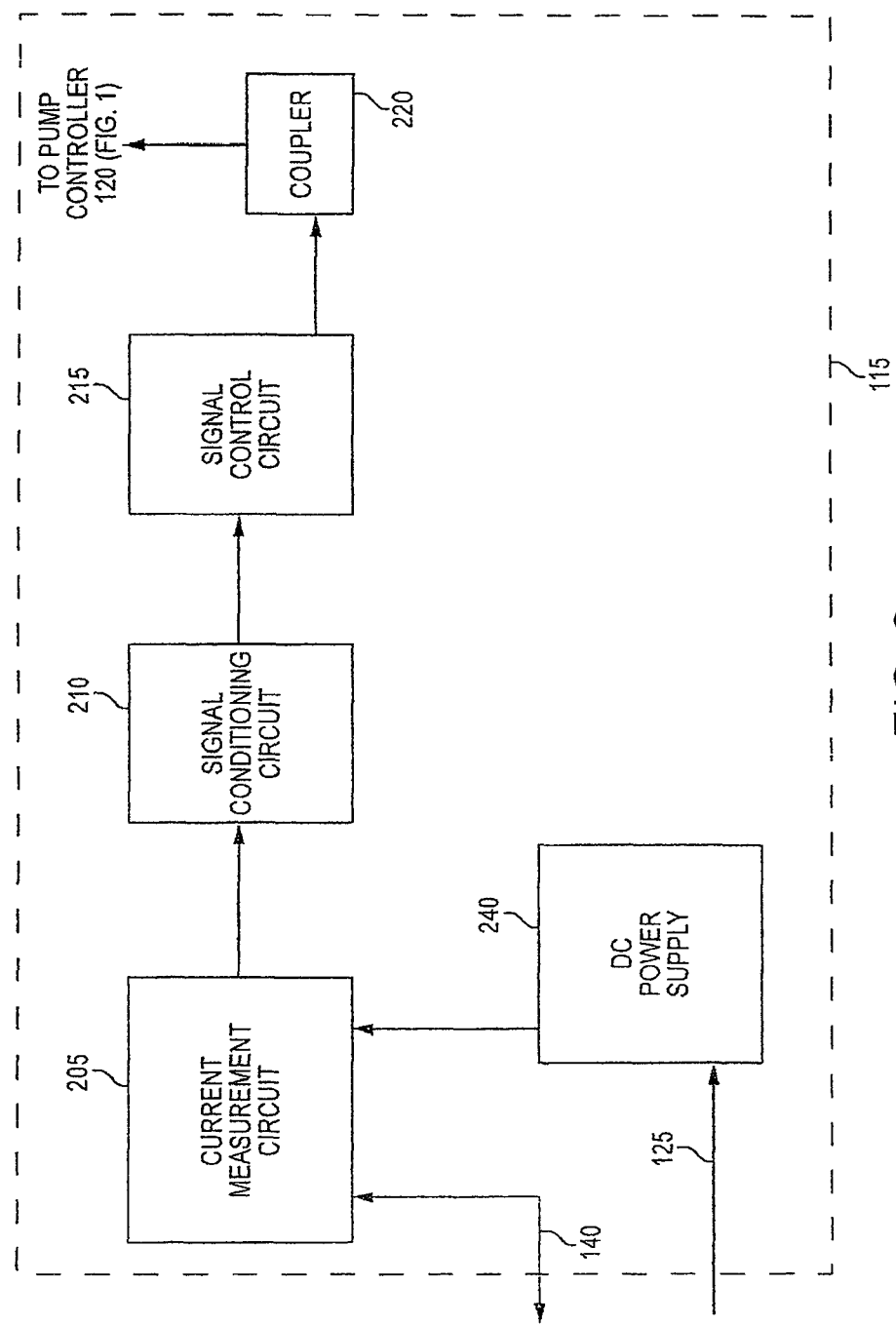
FIG. 2A illustrates a block diagram of the detection circuit of the fluid management system of FIG. 1, in accordance with an exemplary embodiment of the invention.

FIG. 2A illustrates a block diagram of detection circuit 115 of FIG. 1, in accordance with one exemplary embodiment of the invention. Detection circuit 115 includes a current measurement circuit 205 that monitors the change in current load being supplied to the surgical device. AC power that is used by the surgical device (i.e., at console 105 of FIG. 1) is measured by current measurement circuit 205. Current measurement circuit 205 is electrically isolated from the inflow/outflow pump components of fluid management system 100, and galvanically isolates the current provided to power cord 140.

When the surgical device is not being operated, a non-operational current level being supplied to console 105 is measured by detection circuit 115. However, when the surgical device is being operated, a higher level of current (i.e., higher than the non-operational current level) is measured by detection circuit 115 as being supplied to the shaver console 105.

FIG. 2A also depicts power supply 240. Power supply 240 may receive power via separate power cord 125, or from the inflow/outflow pump power supply 130. In one embodiment, detection circuit 115 is separate and external to the inflow/outflow pump components of fluid management system 100, and power supply 240 receives power via separate power cord 125. In another embodiment, detection circuit 115 is internal to the inflow/outflow pump components of fluid management system 100, and receives power from the DC supply used to power circuitry of the inflow-outflow pump components, such as pump control circuit 120 (FIG. 1).

In either case, current measurement circuit 205 is preferably electrically isolated from DC power supply 240 to prevent interference with the detected current being provided to the surgical device. For example power supply 240 may include DC-to-DC converters acting as isolating voltage regulators to galvanically isolate power provided from the DC supply used to power circuitry of the inflow-outflow pump components. Power supply 240 may also include a transformer to galvanically isolate power provided by a separate source (i.e., separate power cord 125), or to further galvanically isolate power provided internally. In accordance with one embodiment, when detection circuit 115 is external to the inflow/outflow pump components of fluid management system 100, the transformer decouples the detection circuit's DC signals from the power supply of the surgical device, and is where DC supply signals for detection circuit 115 are generated, rectified, and provided to the components.

Power cord 140, which provides power to the attached surgical device (FIG. 1), is coupled to current measurement circuit 205. Detection circuit 115 continually monitors the surgical device's current consumption. Current measurement circuit 205 (either constantly or repeatedly) generates a signal according to the amount of current provided to power cord 140. For example, when an attached surgical device is operational (i.e., hand piece 110 of FIG. 1 is turned on), current consumption by the surgical device (i.e., from power cord 140 to console 105 of FIG. 1) increases in order to supply power for operation. The signal is fed by the current measurement circuit 205 through a signal conditioning circuit 210. Signal conditioning circuit 210 generates a linear DC voltage between 0 and 5 volts representing the amplitude of the signal from the current measurement circuit 205, which in turn represents the current consumption of the surgical device. Signal conditioning circuit 210 provides the linear DC voltage to an input of signal control circuit 215, which can be, for example, a micro-controller. Signal control circuit's 215 input may also include an analog-to-digital converter for converting the linear DC voltage to a digital voltage value. This digital voltage value may then be compared to a baseline value to determine the operational status of the surgical device, as well as to identify the manufacturer and/or part number of the surgical device, as further described below.

Signal control circuit 215 then generates an appropriate signal via coupler 220. The signal is provided to pump control circuit 120 (see FIG. 1), which controls the outflow and/or inflow operations of the fluid management system 100 according to whether the surgical device is being operated. (A separate signal identifying the surgical device may also be sent to pump control circuit 120, if so determined.) Coupler 220 is configured to provide a signal between detection circuit 115 and pump control circuit 120 while maintaining electrical isolation between the two components.

Coupler 220 may be, for example, an optocoupler that produces a logic signal, with an input that is electrically isolated from its output. In one embodiment, signal control circuit 215 contains a logic pin that is normally at ground, meaning that the input of coupler 220 is also at ground. However, coupler 220 may use a logic "NOT," resulting in the output of the coupler 220 being logic high (i.e., 5 volts DC). When the logic pin of signal control circuit 215 switches to a logic high (i.e., 5 volts DC), indicating increased power being provided to the surgical device, the output side of coupler 220 switches to logic low. The logic signal from detection circuitry 115 is provided to pump control circuit 120 (FIG. 1), described further below.

Figure 2B:
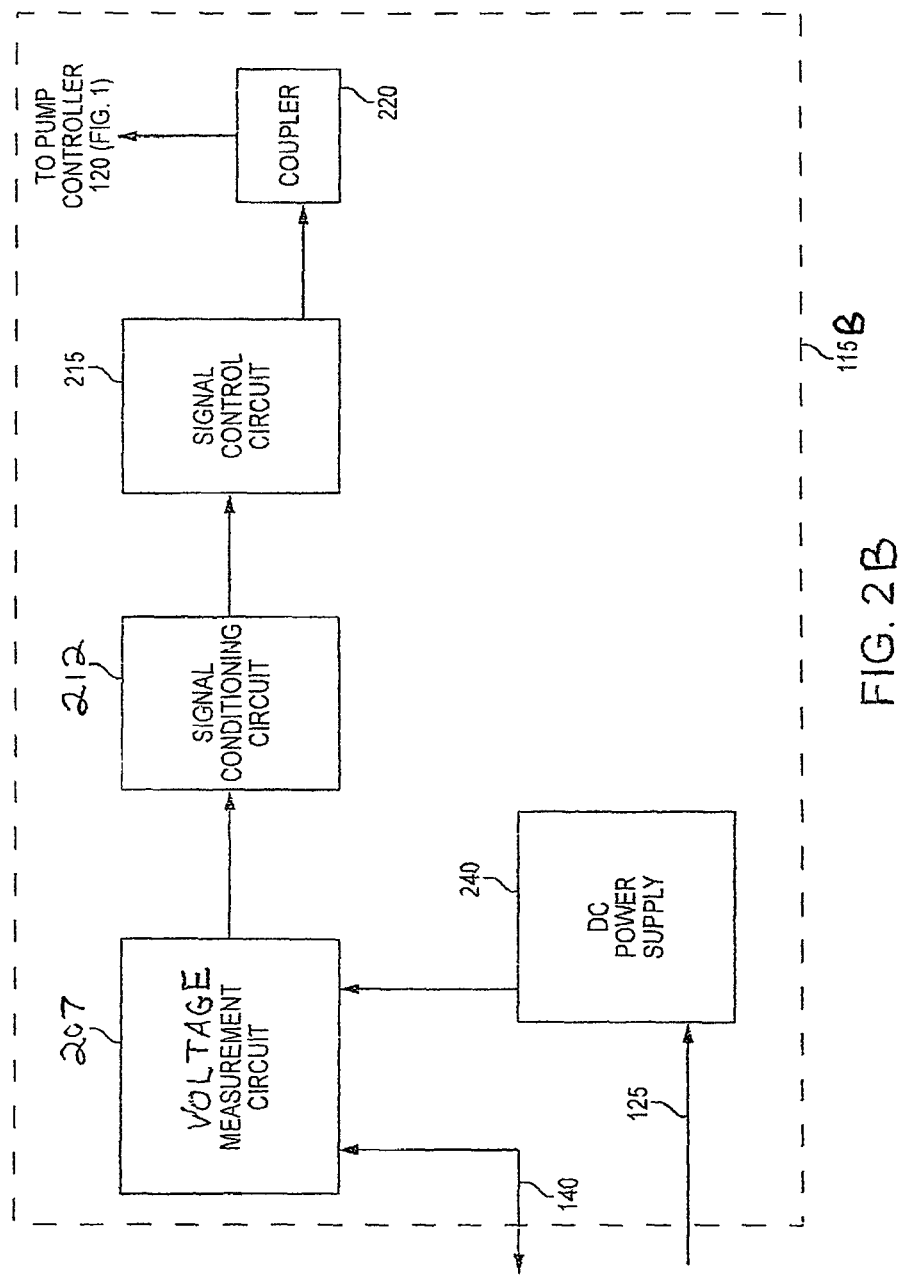
FIG. 2B illustrates a block diagram of the detection circuit of the fluid management system of FIG. 1, in accordance with another exemplary embodiment of the invention.

FIG. 2B illustrates a block diagram of a detection circuit in accordance with another exemplary embodiment of the invention. Detection circuit 115B shown in FIG. 2B is similar to detection circuit 115 shown in FIG. 2A, and like reference numbers designate like elements. Detection circuit 115B, however, includes voltage measurement circuit 207 and signal conditioning circuit 212, rather than, or in addition to, current measurement circuit 205 and signal conditioning circuit 210 of FIG. 2A. In FIG. 2B, power cord 140, which provides power to the attached surgical device (FIG. 1), is coupled to voltage measurement circuit 207. Voltage measurement circuit 207 monitors the change in voltage at the interface to power cord 140.

Although detection circuits 115 and 115B include current measurement circuit 205 and voltage measurement circuit 207, respectively, detection circuit 115 may instead (or additionally) include circuits designed to measure other signal characteristics. For example, detection circuit 115 may also include a noise measurement circuit designed to measure the noise level of the AC signal provided to power cord 140. It should be understood that many known AC signal characteristics and corresponding circuits for measuring these AC signal characteristics are known in the art, and any such circuit for measuring an AC signal characteristic may be used with the detection circuit described above.

In addition, multiple signal characteristics may be measured for detection. For example, it should also be noted that the accuracy of detection circuit 115 and/or 115B can be improved upon by monitoring both the current provided to the surgical device and the power cord voltage level. The power usage of the surgical devices can be calculated by using both monitored current and voltage levels. By using the calculated power, deviations in line voltage can be filtered out and, and false current surges can be eliminated.

When the surgical device is not being operated, a non-operational voltage level at the interface to power cord 140 is measured by detection circuit 115. However, when the surgical device is being operated, a higher level of voltage (i.e., higher than the non-operational voltage level) is measured by detection circuit 115 at the interface to power cord 140. Signal conditioning circuit 212 generates a linear DC voltage between 0 and 5 volts representing the amplitude of the signal from voltage measurement circuit 207, which in turn represents the voltage consumption of the surgical device.

Figure 3:
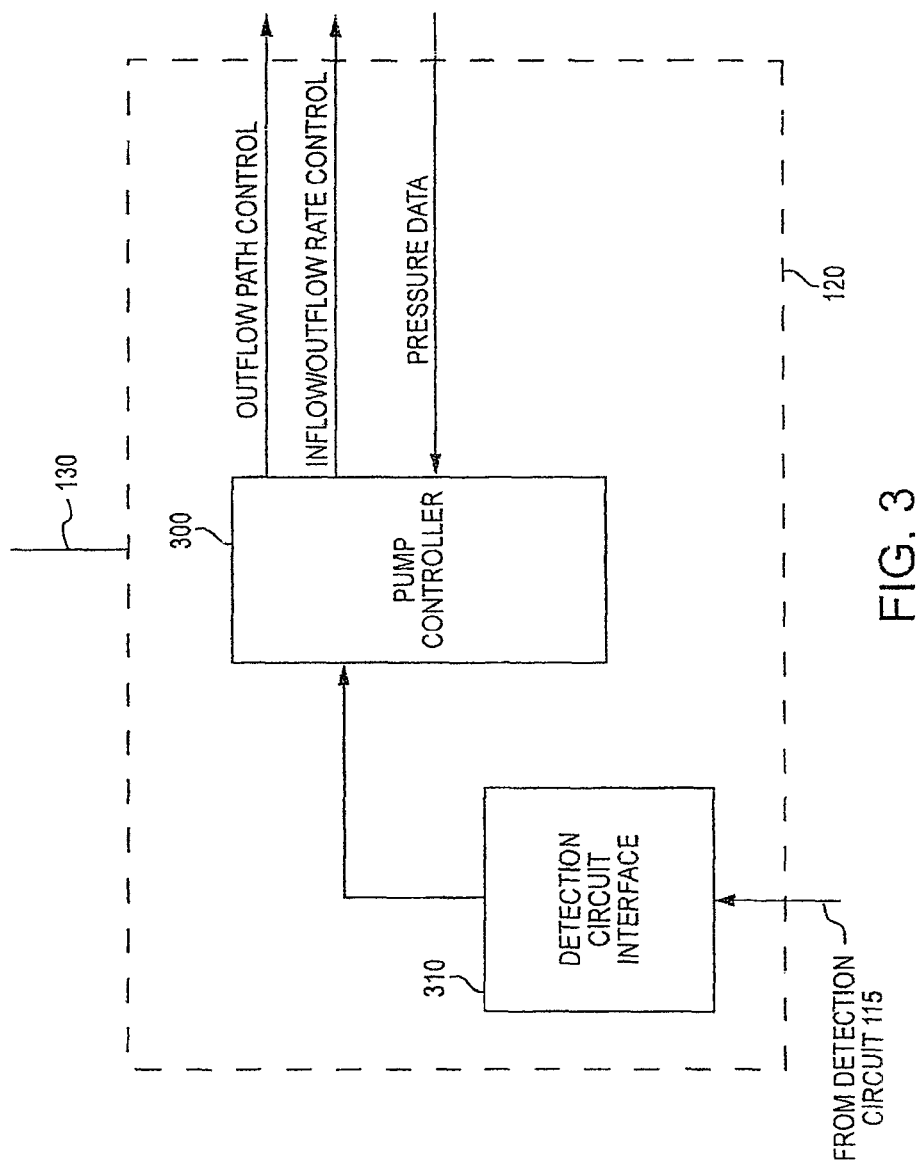
FIG. 3 illustrates a block diagram of the pump control circuit of the fluid management system of FIG. 1, in accordance with an exemplary embodiment of the invention.

FIG. 3 illustrates a block diagram of pump control circuit 120 of the fluid management system 100 (FIG. 1), in accordance with an exemplary embodiment. The isolated signal from detection circuit 115 is provided through a detection circuit interface 310 to pump controller 300. Pump controller 300, which may be a micro-controller, recognizes that the signal went from 5 volts (indicating non-operational status of the surgical device) to ground (indicating operational status). The pump control circuit 120 in turn switches the outflow of the inflow/outflow pump to the operational outflow path (i.e., the device tube), adjusts the speed of the motors controlling pressure of the outflow and/or inflow tubes to increase or decrease the flow rate, adjusts the inflow pressure, adjusts a pressure algorithm (discussed further below) and/or adjusts other operation modes of fluid management system 100.

Figure 4:
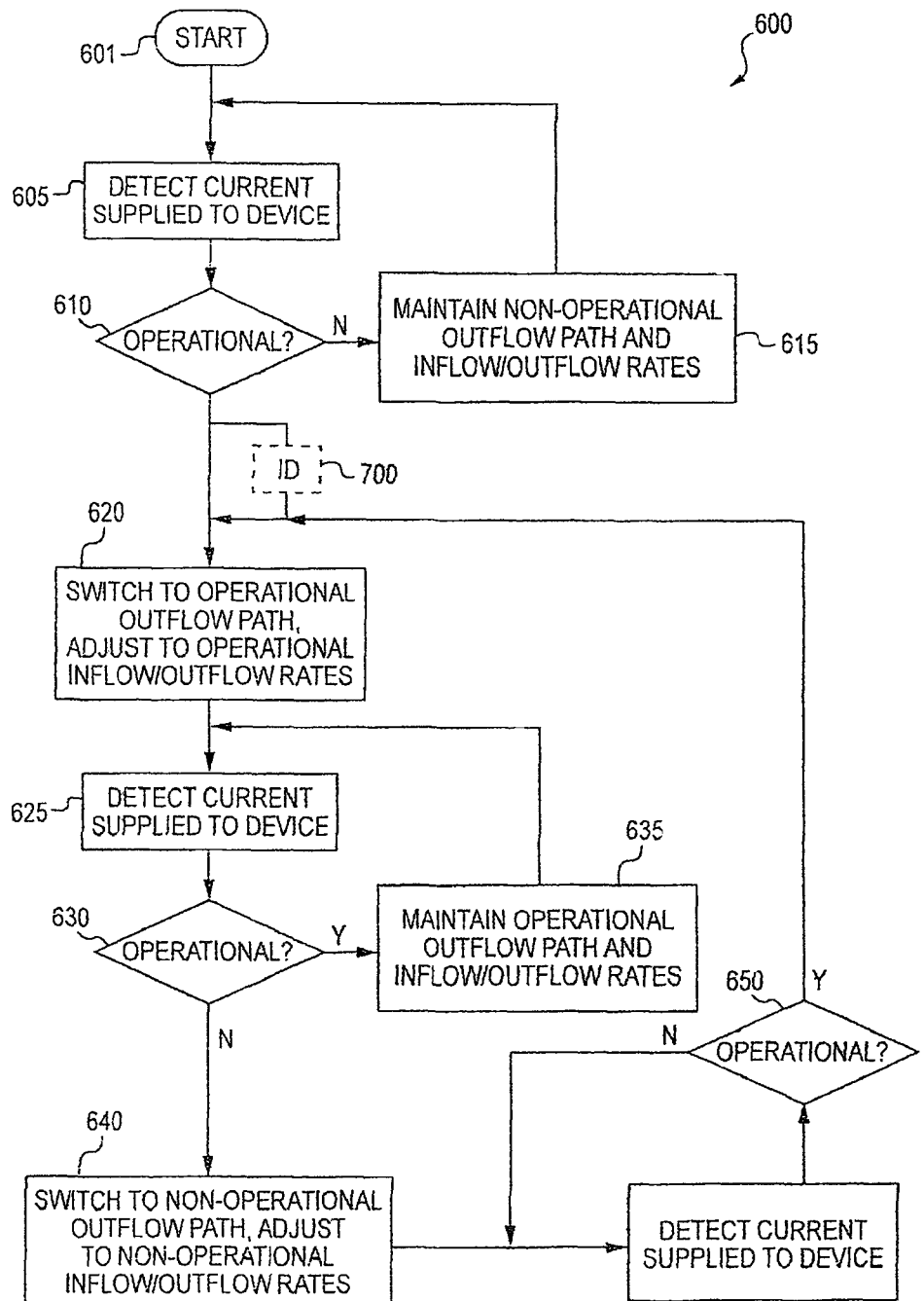
FIG. 4 illustrates a flow diagram of a method for controlling the fluid management system of FIG. 1, in accordance with an exemplary embodiment of the invention.

FIG. 4 illustrates a flow diagram of a method 600 for controlling the fluid management system 100 of FIG. 1, in accordance with an exemplary embodiment. Although for purposes of clarity, method 600 shows monitoring current levels, it should be understood that the steps of method 600 could include monitoring other signal characteristics, instead of or in addition to, current level. For example, in steps 605, 625, and 645, a voltage level at the interface of the fluid management system 100 may be detected, rather than a current level. Alternatively, both voltage and current levels, or other signal characteristics, could be detected.

Method 600 begins at step 601. At step 605, signal characteristics such as the current level being supplied to the surgical device are detected by detection circuit 115 (FIG. 1), as described above. At step 610, a determination is made whether the surgical device is being operated. If not, the non-operational outflow path (i.e., the cannula tube) and non-operational flow rates are maintained, as shown at step 615. If it is determined that the surgical device is being operated, however, the outflow path is switched to the operational outflow path (i.e., the device tube) and the inflow and/or outflow rates also may be increased to an operational level at step 620.

In addition, other operation modes of fluid management system 100 may be changed accordingly at step 620. For example, as further described below, a pressure algorithm for determining the pressure at the operative site may also be adjusted accordingly. The pressure algorithm may be adjusted by changing variables and factors within the algorithm known to vary according to increases or decreases in inflow and/or outflow rate, or by using different algorithms known to produce more accurate estimates at different flow rates according to the detected operational status of the surgical device and/or the detected flow rate set by pump control circuit 120.

Additionally, prior to switching the outflow path and inflow/outflow rates at step 620, the manufacturer and/or part number of the attached surgical device may be determined at step 700, and the identified surgical device's optimal inflow/outflow rates set in the pump control, as further described below with regard to FIG. 5.

Returning to FIG. 4, at step 625, signal characteristics (such as current level) are again detected, and at step 630, a determination is made as to whether the surgical device remains in an operational state. If so, the operational outflow path and flow rates are maintained, as shown at step 635, and the determination of step 630 is made again after a predetermined amount of time. If the operational status has changed (i.e., the shaver is detected as being non-operational), then at step 640, the outflow path is switched to the non-operational path (i.e., the cannula tube), the inflow and/or outflow rates are decreased to the non-operational flow rate, and/or other operation modes are adjusted accordingly.

At steps 645 and 650, signal characteristics are again detected and a determination is made whether the surgical device has switched to an operational state. If not, the non-operational operation modes are maintained, and the determination is made again after a predetermined time. If the operational status has changed (i.e., the shaver is detected as being non-operational), then the flow diagram returns to step

620. Alternatively, the flow diagram may return to step 700 (identifying the attached surgical device).

Figure 5:
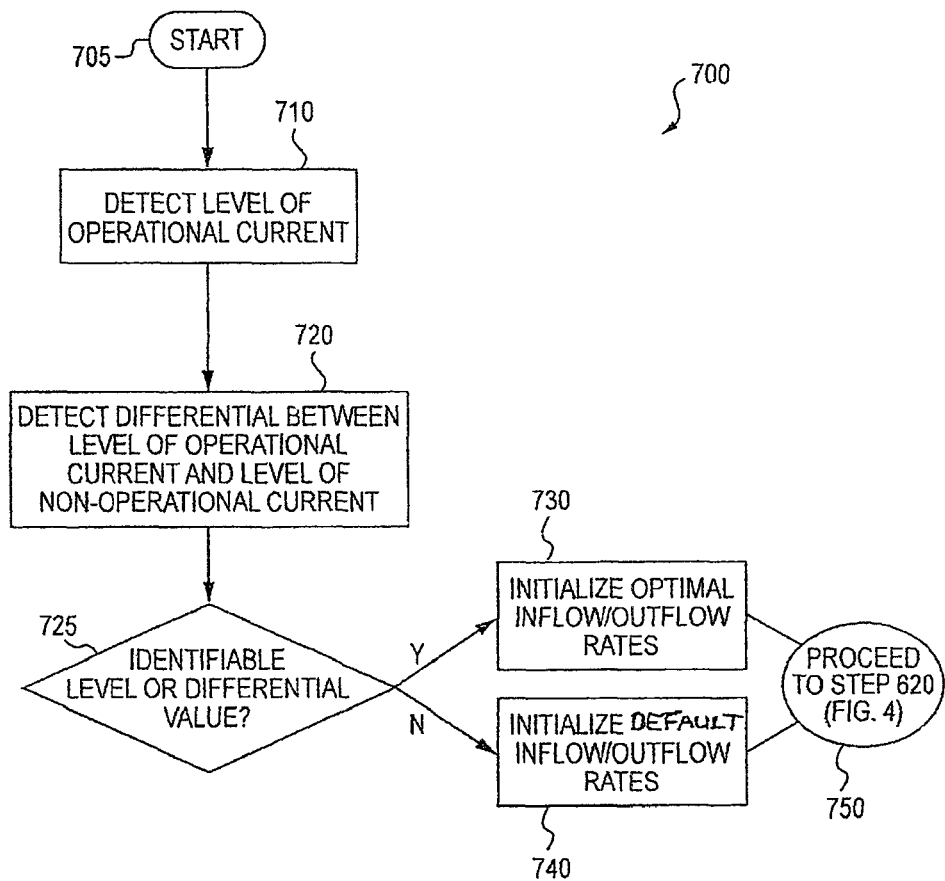
FIG. 5 illustrates a flow diagram of a method for controlling another aspect of the fluid management system of FIG. 1, in accordance with an exemplary embodiment of the invention.

FIG. 5 illustrates a flow diagram of a method 700 for identifying the surgical device attached to the fluid management system 100 of FIG. 1, in accordance with another exemplary embodiment. Although for purposes of clarity, method 700 shows monitoring current levels, it should be understood that the steps of method 700 and discussed below could include monitoring other signal characteristics, instead of or in addition to, current level. For example, in steps 710 and 720, a voltage level at the interface of the fluid management system 100 and a voltage differential may be detected, rather than a current level. Alternatively, both voltage and current levels, or other signal characteristics, could be detected.

The method begins at step 705, which, as discussed above, occurs after step 610 and prior to step 620 of FIG. 4. At step 710, operational signal characteristic levels—such as the level of operational current being supplied via power cord 140 (FIG. 1)—are detected. At step 720, a differential between operational and non-operational levels of one or more signal characteristics may also be detected. For example, as shown in FIG. 5, the differential between the level of operational current detected at step 710 and the non-operational current level detected at step 605 of FIG. 4 may be determined. Both the operational signal characteristic level(s) and the differential(s) of the attached surgical device can be used to identify the manufacturer and/or part number of the attached surgical device.

At step 725, it is determined whether the detected operational signal characteristic level(s) and/or differential(s) are known, such that they identify a particular manufacturer and/or part number of the attached surgical device. If so, as shown at step 730, known optimal inflow/outflow rates for the attached surgical device may be set in the pump control circuit 120 (FIG. 1). If the detected values are not identifiable, as shown at step 740, default inflow/outflow rates that are generally compatible with most surgical devices may be set in the pump control circuit 120. (These default values may be automatically set in pump control circuit 120 prior to the determination in method 700; in such a case, no change in the values is needed at step 740.) At step 750, the method proceeds to step 620 of method 600 (FIG. 4).

Figure 6:
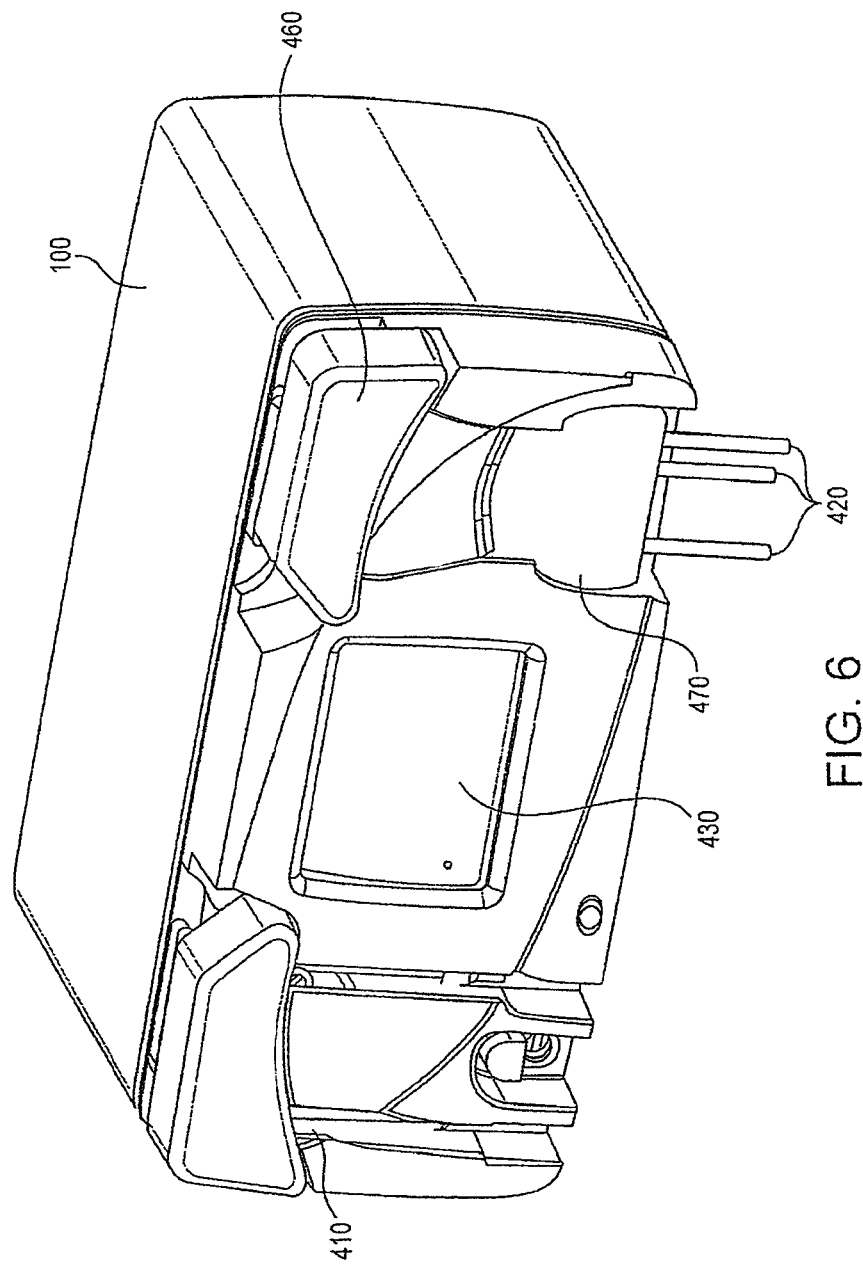
FIG. 6 illustrates a front view of a fluid management system, in accordance with an exemplary embodiment of the invention.
Figure 7:
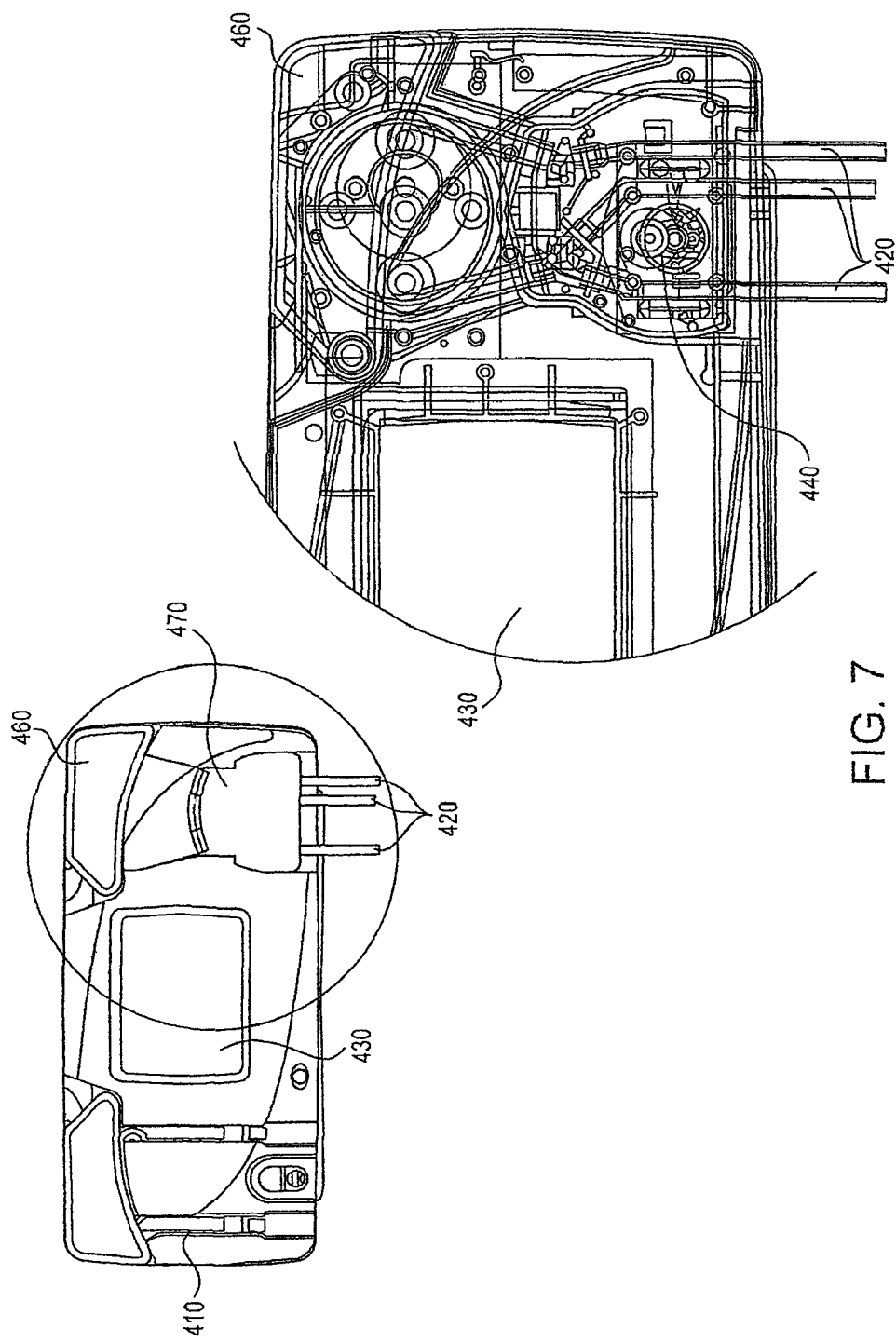
FIG. 7 illustrates a close-up front view of a fluid management system, in accordance with an exemplary embodiment of the invention.
Figure 8:
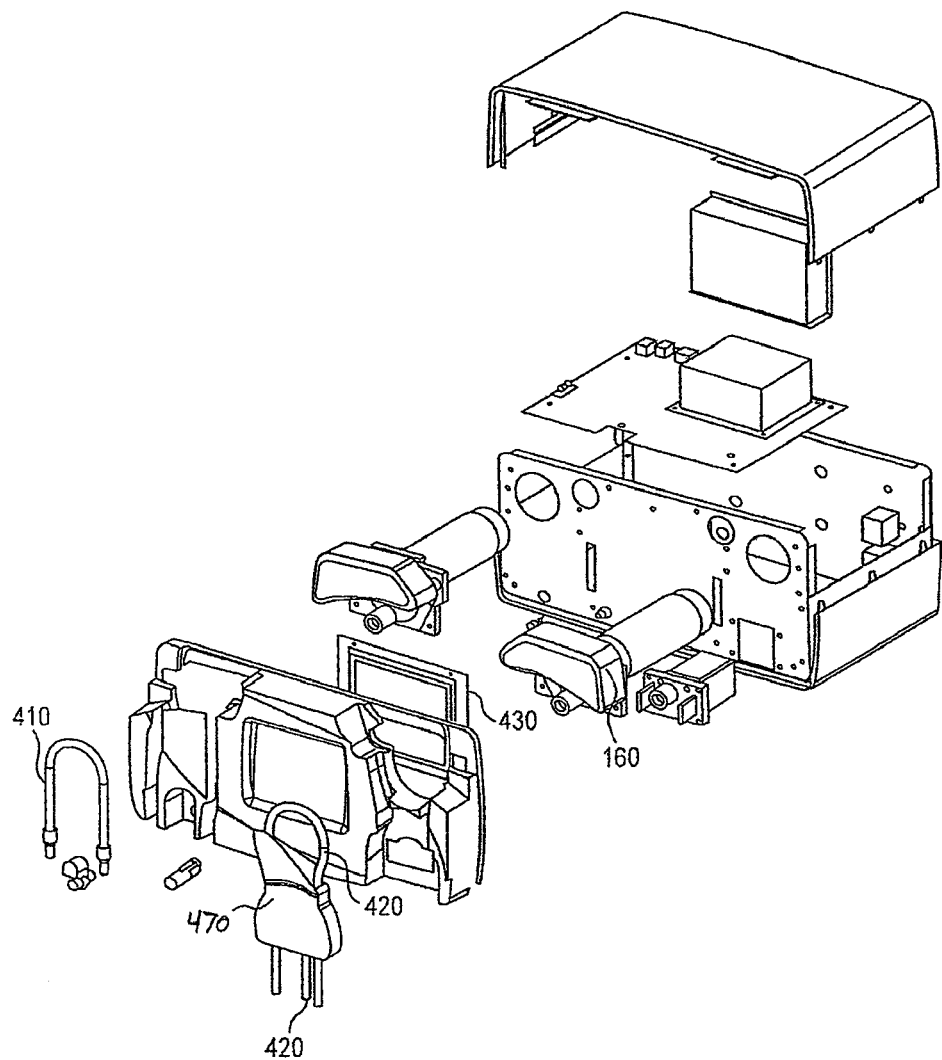
FIG. 8 illustrates an exploded view of a fluid management system, in accordance with an exemplary embodiment of the invention.

FIGS. 6-8 depict different views of the exterior of the fluid management system 100, in accordance with an exemplary embodiment of the invention. The exterior includes the inflow fluid pathway 410, outflow fluid pathways 420, and a display portion 430 for displaying flow rates and other operational parameters. The exterior also includes outflow door 460 and cassette 470, described further below. Although not shown here, the exterior of the fluid management system 100 also includes power cord 130 (see FIG. 1).

FIG. 7 shows, inter alia, a pinch mechanism 440 for switching between the operational and non-operational outflow paths. Fluid management system 100 may also include a pinch mechanism (not shown) for the inflow fluid pathway 410. Pinch mechanism 440 includes a wheel attached to a rotating motor, such as a stepper motor.

It is often necessary to replace the tubes of the outflow pathway 420 (i.e., the device and cannula tubes), due to the type of liquid being delivered or wear on the tubes. In the embodiment shown in FIG. 7, the rotary motor of the pinch mechanism 440 moves to the center of its axis during replacement of the outflow tubes. This feature eases setup of the fluid management system 100. While mechanisms of conventional fluid management systems remain aligned to pinch off one of the outflow tubes, pinch mechanism 440 positions the wheel so as not to restrict any of the outflow tubes. Pinch mechanism 440 can be configured to rotate to its center axis whenever the outflow door 460 is opened. A stepper motor provides precise angular rotation to allow accurate positioning of the wheel.

Pinch mechanism 440 provides an advantageous configuration for installing and replacing the tubes of the outflow pathways 420. Because pinch mechanism 440 frees all of the tubes of the outflow pathways 420 during replacement of the outflow tubes (for example, when outflow door 460 is opened), the user can attach or detach a cassette 470 that contains all outflow tubes, rather than threading individual tubes into fluid management system 100.

Figure 9:
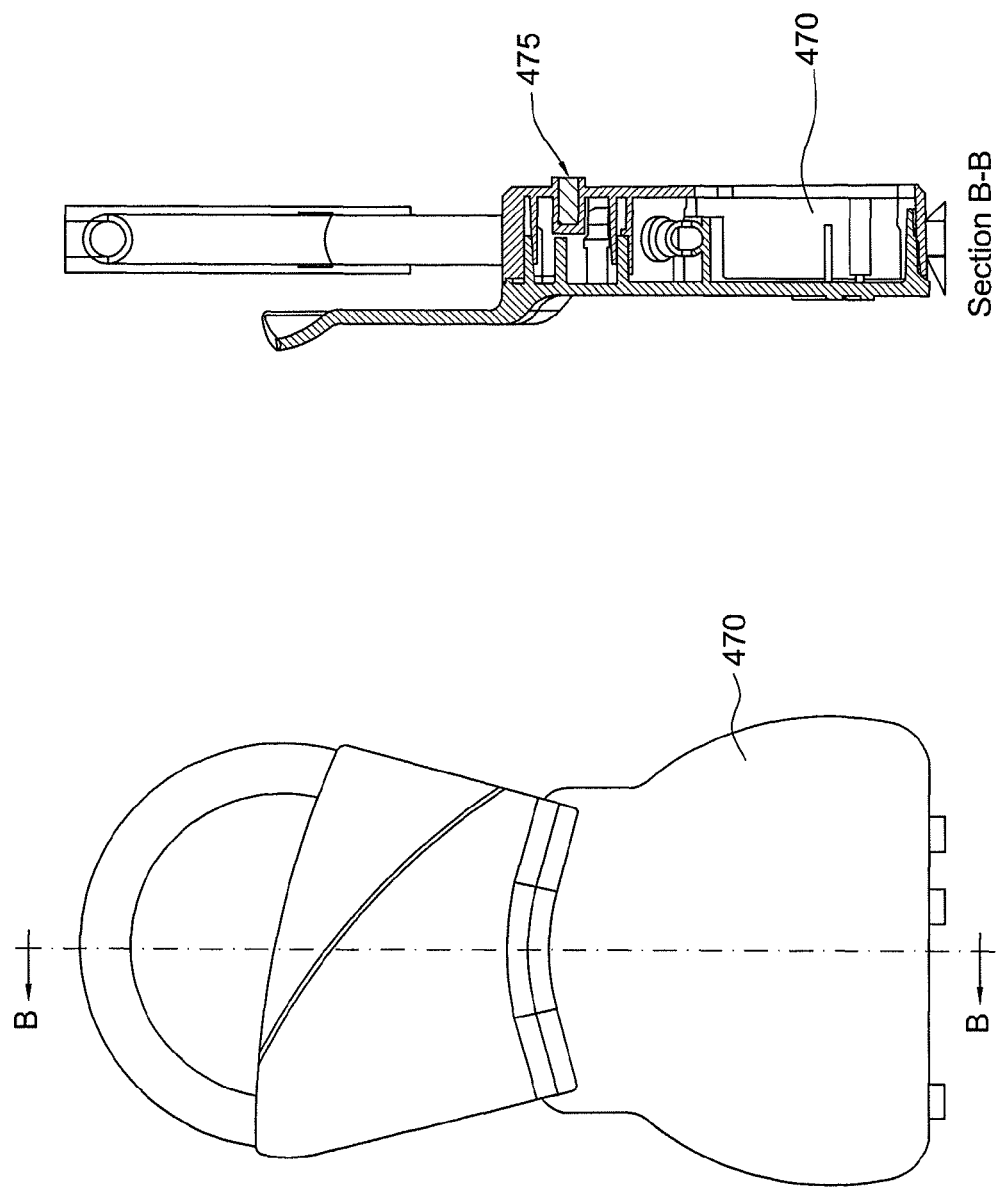
FIG. 9 illustrates a front view and a cross-sectional view of a cassette for a fluid management system, in accordance with an exemplary embodiment of the invention.

FIG. 9 illustrates a front view and a cross-sectional view of a cassette 470 for use with fluid management system 100, in accordance with an exemplary embodiment of the invention. As shown in FIG. 9, cassette 470 can include a sensible element 475. Sensible element 475 may be, for example, a metal pin that can be detected magnetically. Alternatively, sensible element 475 may be a radio-frequency identification (RFID) device or other identifiable device that can be detected with radio waves, infrared waves, or other known methods.

Figure 10:
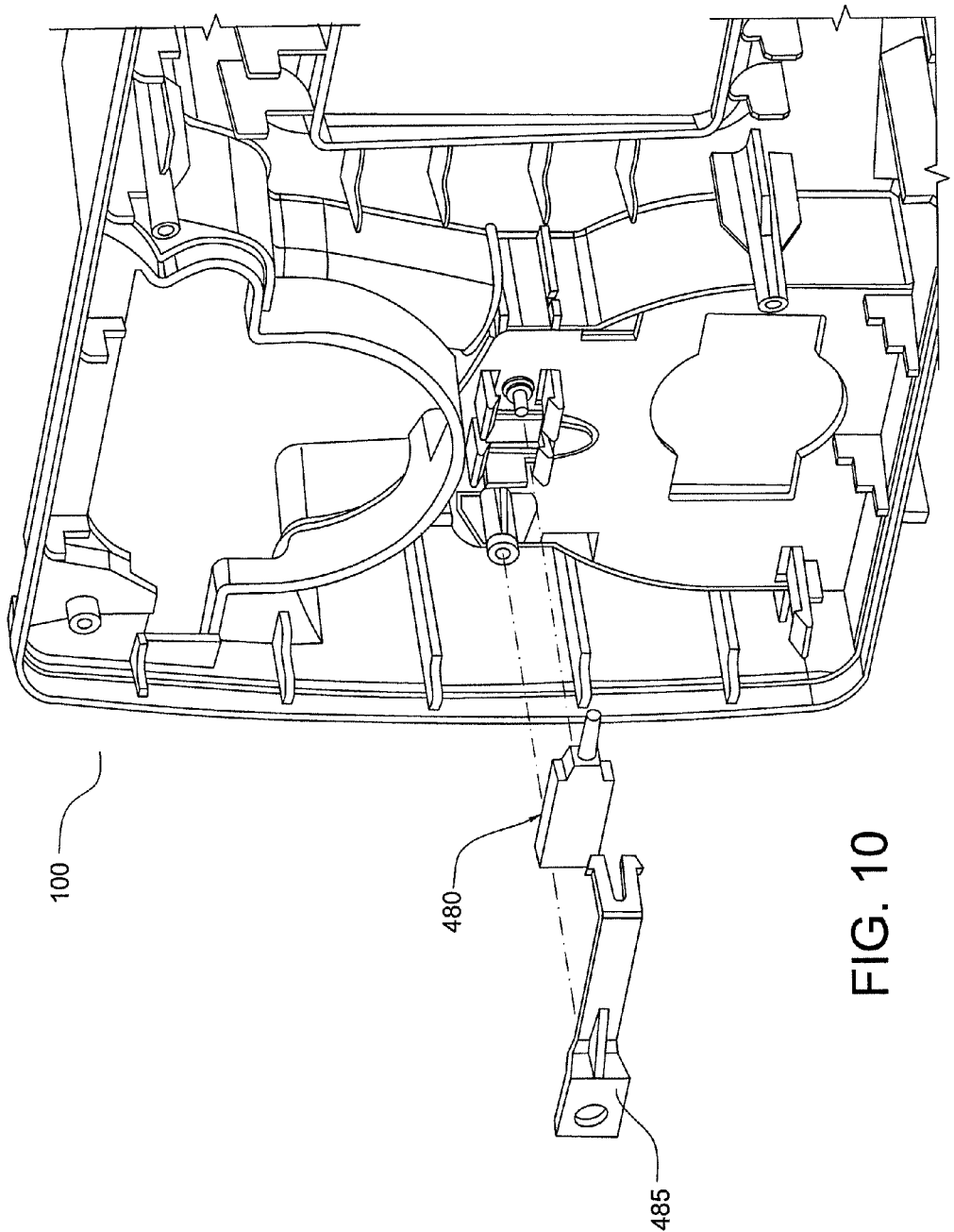
FIG. 10 illustrates an exploded rear view of a section of a fluid management system, in accordance with an exemplary embodiment of the invention.

FIG. 10 illustrates an exploded rear view of a section of fluid management system 100, in accordance with an exemplary embodiment of the invention. As shown, fluid management system 100 includes cassette sensor 480, which may be mounted in place by a bracket 485. Cassette sensor 480 is configured to detect the presence of sensible element 475 (FIG. 9), and may be a sensor configured to detect the presence of metal, or a frequency-sensitive device such as an RFID sensor.

Cassette sensor 480 can be used to authenticate cassettes used with fluid management system 100. Pump control circuit 120 can be used to monitor a signal output by cassette sensor 480, and until cassette sensor 480 detects the presence of sensible element 475, pump control circuit 120 can be configured to enable or not perform the outflow operations of fluid management system 100. Alternatively, pump control circuit 120 can be configured to disable both inflow and outflow operations until the presence of sensible element 475 is detected. In other words, if fluid management system 100 does not detect the presence of the sensible element 475, the inflow/outflow pump will not run. In addition, the signal from cassette sensor 480 can be used to ensure that the cassette 470 is correctly loaded in place in fluid management system 100 before allowing operation.

Fluid management system 100 can also be configured to estimate the fluid pressure at the operative site. For example, the pressure at the output of the inflow path 210 (FIG. 6) can be measured and used to estimate the fluid pressure at the operative site using a pressure algorithm. It should be understood, however, that the embodiments described herein are not limited to this method of estimation, and can be applied to any known process for estimating a pressure level.

Referring back to FIG. 3, pump control circuit 120 receives pressure data at the pump controller 300 from a pressure sensor at the inflow pathway 210 of fluid management system 100 (FIG. 4). Conventional estimation techniques assume that the pressure at the operative site remains in a constant relationship (e.g., proportional) to the pressure measured at the inflow path 210. Thus, conventional estimation techniques use a static technique, applying the same pressure algorithm during both operational and non-operational states of the fluid management system 100, and when differing flow rates are used.

As the flow rate increases, however, the relationship between the inflow pressure and actual pressure at the operative site does not remain constant. Rather, the actual pressure increases non-linearly versus the detected pressure as the flow rate of the inflow/outflow pump increases (such as when the surgical device is operational). Thus, it is beneficial to adjust the pressure algorithm used to estimate the pressure at the operative site as the flow rate increases (i.e., dynamically), and vice versa.

Dynamic calculation of the pressure at the operative site using real time flow rates produces higher accuracy results. Applicants have observed that, when the system flow rate approaches zero, the measured pressure at the pump approximately equals the pressure at the operative site. As flow rate increases, however, the pressure at the operative site is less than the measured pressure at an increasing rate. Thus, using such a dynamic method provides a better representation of the actual pressure at the operative site—i.e., the physiological joint pressures.

In one embodiment, when detection circuit 115 (FIG. 1) provides a signal to pump control circuit 120 indicating that the surgical device is operational, in addition to changing other operational modes of fluid management system 100, pump control circuit 120 can adjust the pressure algorithm used to convert the received inflow pressure data to estimated pressure data. The pressure algorithm may be adjusted for operational and non-operational states and according to the flow rates of these operational and non-operational states.

Figure 11:
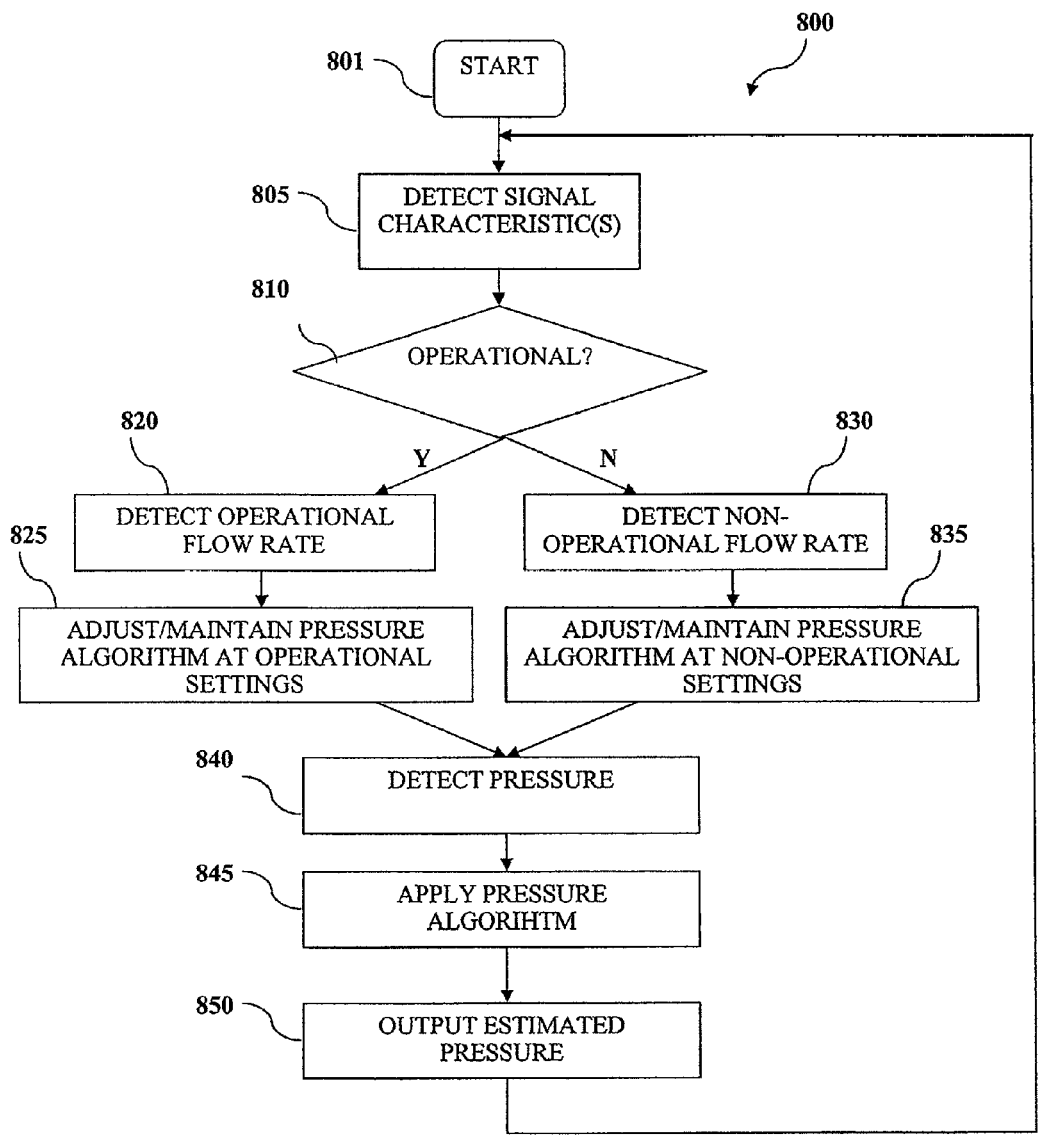
FIG. 11 illustrates a flow diagram of a method for controlling another aspect of a fluid management system, in accordance with an exemplary embodiment of the invention.

FIG. 11 illustrates a flow diagram of a method 800 for adjusting a pressure algorithm of a fluid path (which may be an inflow fluid path, outflow fluid path, or both) in a fluid management system, in accordance with an exemplary embodiment of the invention. The method begins at step 801, which may take place upon power-up of the fluid management system, or at any time after. At step 805, one or more signal characteristics are detected, and at step 810 a determination is made whether the attached device is in an operational state, in accordance with methods and apparatuses discussed above.

If the attached device is determined to be in an operational state, in step 820 pump controller 300 (FIG. 3) may detect (or read from memory) the operational flow rate of the fluid path. (Detection of the flow rate may instead occur after adjusting the pressure algorithm between operational and non-operational settings, or not at all.) In step 825, the pressure algorithm either remains or is adjusted to its operational settings. This may include adjusting variables or equations used to calculate the estimated pressure value from the detected pressure value.

If instead the attached device is determined to be in a non-operational state, in step 830 pump control circuit 120 may detect the non-operational flow rate, in similar manner to detection of the operational flow rate, as discussed above. At step 835, the pressure algorithm either remains or is adjusted to its non-operational settings.

After detecting the operational state of the attached device and adjusting the pressure algorithm accordingly, at step 840 the pressure of the fluid path is detected. At step 845, the pressure algorithm is applied to the detected pressure to calculate an estimated pressure, representing the pressure at the operative site. At step 850, the estimated pressure is output, for example to display 430 (FIG. 6).

It should be understood that the pressure algorithm may be applied by pump controller 300 (FIG. 3), which may be a circuit such as a micro-controller, an ASIC, or a programmable integrated circuit. The pressure algorithm may also be applied by another circuit in or external to pump control circuit 120. The pressure algorithm may be implemented via hardware or software, or a combination of both. In addition, it should be understood that the above-described method of estimating pressure is but one example of a method of estimating pressure at an operative site using a pressure algorithm, and the adjustment of a pressure algorithm according to operational states and/or flow rates is not so limited to use with this method of estimating pressure. Further, method 800 may be applied for purposes of estimating pressure or other variables at sites other than an operative site.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description, but only by the appended claims.

What is claimed as new and desired to be protected by Letters Patent of the United States is:

1. A device for controlling a direction of a fluid path of a fluid management system, said mechanism comprising:
   a rotating motor;
   a wheel attached to the rotating motor to restrict a first tube of said fluid path when said rotating motor rotates to one of a first and second position and a second tube of said fluid path when said rotating motor rotates to the other of said first and second positions,
   wherein said rotating motor is configured to rotate to a third position during replacement of said first and second tubes; and
   a cassette holding the first and second tubes, the cassette being attachable to and detachable from the fluid management system, wherein the rotating motor is configured to rotate to a center of its axis during loading and unloading of the first and second tubes.

2. The device of claim 1, wherein said rotating motor is a stepper motor.

3. The device of claim 1, wherein said rotating motor is a stepper motor and said third position is the center of the rotating motor's axis.

4. The device of claim 1, wherein said rotating motor is configured to rotate to said third position during attachment or detachment of said cassette.

5. The device of claim 1, said cassette further comprising a sensible element detectable by said fluid management system, wherein said fluid management system is configured to not operate said fluid path unless said sensible element is detected.

6. The fluid management system of claim 5, wherein said sensible element is a metal pin.

* * * * *